US009415064B2

(12) United States Patent
Hraschan

(10) Patent No.: US 9,415,064 B2
(45) Date of Patent: Aug. 16, 2016

(54) PREVENTION OR TREATMENT OF PAINFUL POLYNEUROPATHIES BY ADMINISTRATION OF AN ALUMINOSILICATE

(71) Applicant: Jakob Hraschan, Gödersdorf (AT)

(72) Inventor: Jakob Hraschan, Gödersdorf (AT)

( * ) Notice: Subject to any disclaimer, the term of this patent is extended or adjusted under 35 U.S.C. 154(b) by 275 days.

(21) Appl. No.: 14/115,087

(22) PCT Filed: Dec. 4, 2012

(86) PCT No.: PCT/EP2012/074345
§ 371 (c)(1),
(2) Date: Oct. 31, 2013

(87) PCT Pub. No.: WO2013/098049
PCT Pub. Date: Jul. 4, 2013

(65) Prior Publication Data
US 2014/0057000 A1 Feb. 27, 2014

(30) Foreign Application Priority Data
Dec. 30, 2011 (EP) ..................................... 11196189

(51) Int. Cl.
*A61K 33/06* (2006.01)
*A61K 45/06* (2006.01)

(52) U.S. Cl.
CPC ................. *A61K 33/06* (2013.01); *A61K 45/06* (2013.01)

(58) Field of Classification Search
CPC ..................................................... A61K 33/06
See application file for complete search history.

(56) References Cited

U.S. PATENT DOCUMENTS

2004/0175436 A1* 9/2004 Basic .................. A61K 36/185
424/684

FOREIGN PATENT DOCUMENTS

| WO | 01/95920 A1 | 12/2001 |
| WO | 03/013563 A2 | 2/2003 |
| WO | 2007/054085 A2 | 5/2007 |
| WO | 2011007794 A1 | 1/2011 |

OTHER PUBLICATIONS

Wilsey B, Marcotte T, Tsodikov A, Millman J, Bentley H, Gouaux B, Fishman S J. Pain 9 (6) (2008) 506-21.
Liu N, Varma S, Tsao D, Shooter EM, Tolwani RJ. J. Neurosci. Res. 85 (13) (2007) 2863-9.
D. L. Menkes, A Practical Approach to the Treatment of Painful Polyneuropathies, in: T. E. Bertorini (Ed.), Neuromuscular Disorders: Treatment and Management, Chapter 6, Elsevier, 2011 (ISBN 978-1-4377-0372-6).
T. M. Burns, M. L. Maueremann, Clinical Practice 76 (Suppl. 2) (2011) S6-S13.
Broun, et al., Am. J. Clin. Oncol. 16:18-21 (1993).
Macdonald, Neurologic Clinics 9 955-967 (1991).
Casey, et al., Brain 96 69-86 (1973).
Ozols, Seminars in Oncology 16, suppl. 6:22-30 (1989).
Journal of Clinical and Experimental Medicine 203 (1) (2002) 65-69 with English abstract.
Classification of Chronic Pain, International Association for the Study of Pain (IASP) Task Force on Taxonomy IASP Press: Seattle, pp. 209-214, 1994.
Journal of Clinical and Experimental Medicine 189 (10) (1999) 757-762 with English abstract.
Pharmacological interventions such as antidepressants (Clinics and Drug Therapy, 18 (7) (1999) 643-646) with English abstract.
D.I. Abrams et al., "Cannabis in painful HIV-associated sensory neuropathy—A randomized placebo-controlled trial", Neurology, vol. 68, pp. 515-521 (2007).
M. Pappagallo et al., "Newer Antiepileptic Drugs: Possible Uses in the Treatment of Neuropathic Pain and Migraine", Clinical Therapeutics, 25(10), pp. 2506-2538 (2003).
H. Breivik et al., "Assessment of Pain", British Journal of Anasthesia, 101(1), pp. 17-24 (2008).
M. Koltzenburg et al., "Neural Mechanisms of Cutaneous Nociceptive Pain", The Clinical Journal of Pain, 16(3), pp. S131-S138 (2000).
ClinicalTrials.gov, a service of the US National Institutes of Health (http://clincaltrials.gov/ct2/show/NCT00162968), "Escitalopram as a Treatment for Pain in Polyneuropathy", (2007).
J.D. England et al., "Peripheral Neuropathy", The Lancet, vol. 363, pp. 2151-2161 (2004).
B. Frank et al., "Comparison of analgesic effects and patient tolerability of nabilone and dihydrocodeine for chronic neuropathic pain: randomised, crossover, double blind study", BMJ, 336(7637), pp. 1-8 (2008).
A. Hazekamp et al., "Review on clinical studies with cannabis and cannabinoids 2005-2009", Cannabinoids 2010, pp. 1-21 (2010).
D.M. Jin et al., "Effect of transcutaneous electrical nerve stimulation on symptomatic diabetic peripheral neuropathy: A meta-analysis of randomized controlled trials", Diabetes Research and Clinical Practice, 89(1), pp. 10-15 (2010).
A. Dahm et al., "Ultra-stable zeolites—a tool for in-cell chemistry", Journal of Biotechnology, vol. 111, pp. 279-290 (2004).

(Continued)

*Primary Examiner* — Michael B Pallay
(74) *Attorney, Agent, or Firm* — Mintz Levin Cohn Ferris Glovsky and Popeo, P.C.; Peter F. Corless; Christopher R. Cowles

(57) ABSTRACT

Prevention or treatment of painful polyneuropathies caused by toxic agents, i.e. to the prevention, reduction or elimination of the symptoms associated with such polyneuropathies, such as neuropathic pain are disclosed. An aluminosilicate for use in such prevention or treatment, preferably a natural or synthetic zeolite, such as clinoptilolite, is provided. The toxic agent is, in particular, a chemotherapeutic cytotoxic agent.

13 Claims, No Drawings

(56) References Cited

OTHER PUBLICATIONS

Y. Park et al., "Removal of herbicides from aqueous solutions by modified forms of montmorillonite", Journal of Colloid and Interface Science, In Press, Corrected Proof, Available online Sep. 10, 2011 (2013).

"Polyneuropathy", http://www.merckmanuals.com/home/brain_spinal_cord_and_nerve_disorders/peripheral_nerve_disorders/polyneuropathy.html (2013).

D.E. Moulin et al., "Pharmacological management of chronic neuropathic pain—Consensus statement and guidelines from the Canadian Pain Society", Pain Res. Manage., 12(1), pp. 13-21 (2007).

K. Pieber et al., "Electrotherapy for the treatment of painful diabetic peripheral neuropathy: A Review", J. Rehabil. Med., vol. 42, pp. 289-295 (2010).

C. Woolf et al., "Neuropathic pain: aetiology, symptoms, mechanisms, and management", The Lancet, vol. 353, pp. 1959-1964 (1999).

D.C. Turk et al., "Commentary: What should be the core outcomes in chronic pain clinical trails?", Arthritis Research & Therapy, 6(4), pp. 151-154 (2004).

International Search Report for PCT/EP2012/074345 mailed on Jan. 30, 2013.

Written Opinion of the International Searching Authority for PCT/EP2012/074345 mailed on Jan. 30, 2013.

Journal of Clinical and Experimental Medicine 189 (10) (1999) 751-755 with English abtract (7 pages).

* cited by examiner

PREVENTION OR TREATMENT OF PAINFUL POLYNEUROPATHIES BY ADMINISTRATION OF AN ALUMINOSILICATE

FIELD OF THE INVENTION

The invention relates to the prevention or treatment of painful polyneuropathies caused by toxic agents, particularly by chemotherapeutic cytotoxic agents, i.e. to the prevention, reduction or elimination of the symptoms associated with such polyneuropathies, such as neuropathic pain.

BACKGROUND OF THE INVENTION

Pain, an unpleasant sensation often caused by intense or damaging stimuli, is the most common reason for physician consultation in the United States (Turk D C, Dworkin R H. *Arthritis Res. Ther.* 6 (4) (2004) 151-154). It is a major symptom in many medical conditions, and can significantly interfere with a person's quality of life and general functioning (Breivik H, Borchgrevink P C, Allen S M, Rosseland L A, Romundstad L, Hals E K, Kvarstein G, Stubhaug A. *Br J Anaesth.* 101(1) (2008) 17-24).

Pain motivates withdrawal from damaging or potentially damaging situations, protection of a damaged body part while it heals, and avoidance of similar experiences in the future (Lynn B. Cutaneous nociceptors. In: Winlow W, Holden A V. *The neurobiology of pain: Symposium of the Northern Neurobiology Group, held at Leeds on* 18 *Apr.* 1983. Manchester: Manchester University Press; 1984; p. 106). Most pain resolves promptly once the painful stimulus is removed and the body has healed.

Nociceptive pain is caused by stimulation of peripheral nerve fibers that respond only to stimuli approaching or exceeding harmful intensity (nociceptors), classified according to the mode of noxious stimulation; the most common categories being "thermal" (heat or cold), "mechanical" (crushing, tearing, etc.) and "chemical" (iodine in a cut, chili powder in the eyes). However, pain caused by damage or disease or the side-effects of systemic illness, affecting any part of the nervous system involved in bodily feelings (the somatosensory system), known as neuropathic pain and/or peripheral neuropathic pain, irrespectively, being acute or chronic, and often described as "burning", "tingling", "electrical", "stabbing", or "pins and needles", can be a severely debilitating problem for many patients, doctors and care providers. Classified according to the number of nerves affected (Mononeuropathy, Mononeuritis multiplex, Polyneuropathy), or the type of nerve cell affected (motor, sensory, autonomic), or the process affecting the nerves (e.g. inflammation in neuritis) neuropathic pain is caused by numerous diseases like genetic diseases (Friedreich's ataxia, Charcot-Marie-Tooth syndrome), metabolic/endocrine disease (diabetes mellitus, chronic renal failure, porphyria, amyloidosis, liver failure, hypothyroidism), inflammatory diseases (Guillain-Barré syndrome, systemic lupus erythematosis, leprosy, Sjögren's syndrome, Lyme Disease, sarcoidosis) physical trauma (compression, pinching, cutting, projectile injuries, i.e. gunshot wound), strokes including prolonged occlusion of blood flow, electric discharge, including lightning strikes, vitamin deficiency states (Vitamin $B_{12}$, i.e. cyanocobalamin, vitamin A, vitamin E, vitamin $B_1$, i.e. thiamin) and others (shingles, malignant disease, HIV and radiation), and exposure to toxic agents like drugs (vincristine, metronidazole, phenytoin, nitrofurantoin, isoniazid, fluoroquinolones, ethyl alcohol), natural and synthetic toxins heavy metals, excess intake of vitamin $B_6$ (pyridoxine).

Effectively treating peripheral neuropathic pain poses a great challenge for doctors and health care providers as this type of pain often affects a patient's quality of life. A person's ability to carry out everyday tasks can be severely compromised due to pain, and especially chronic pain and as such the patient's personality can change.

There are many treatment strategies for peripheral neuropathic pain and most of them are symptomatic, and currently there is no global consensus concerning the optimal therapeutic strategy for neuropathic pain, despite an increasing number of clinical trials demonstrating successful pain relief with several drugs.

However, the Canadian Pain Society recently published Consensus statement and guidelines (Pain Res. Manag. 2007 12(1) 13-21), where the medications are recommended in the guidelines if their analgesic efficacy was supported by at least one methodologically sound, randomized, controlled trial showing significant benefit relative to placebo or another relevant control group. Recommendations for treatment are based on degree of evidence of analgesic efficacy, safety, ease of use and cost-effectiveness.

Analgesic agents recommended for first-line treatments are certain tricyclic antidepressants such as amitriptyline and anticonvulsants (gabapentin and its more potent and significantly more expensive successor pregabalin). These have the advantage that besides being effective in many cases they are relatively low cost.

Second-line treatments recommended are serotonin-norepinephrine reuptake inhibitors such as duloxetine and topical lidocaine.

Tramadol and controlled-release opioid analgesics are recommended as third-line treatments for moderate to severe pain. Orally, opiate derivatives were found to be more effective than cannabis for most people (Frank B, Serpell M G, Hughes J, Matthews J N, Kapur D *BMJ* 336 (7637) (2008) 119-201).

Recommended fourth-line treatments include cannabinoids such as nabilone (Hazekamp A, Grotenhermen F, Review on clinical studies with cannabis and cannabinoids 2005-2009, *Cannabinoids* 2010, 5 (special issue) 1-21; Abrams D I, Jay C A, Shade S B, Vizozo H, Reda H, Press S, Kelly M E, Rowbotham Mc, Petersen K L *J. Neurology* 68 (7) (2007) 515-21; Wilsey B, Marcotte T, Tsodikov A, Millman J, Bentley H, Gouaux B, Fishman S *J. Pain* 9 (6) (2008) 506-21), methadone and anticonvulsants with lesser evidence of efficacy, such as lamotrigine, topiramate and valproic acid. Treatment must be individualized for each patient based on efficacy, side-effect profile and drug accessibility, including cost.

Further studies are required to examine head-to-head comparisons among analgesics, combinations of analgesics, long-term outcomes, and treatment of pediatric and central NeP.

TENS (Transcutaneous Electrical Nerve Stimulation) therapy may be effective and safe in the treatment of diabetic peripheral neuropathy (Jin D M, Xu Y, Geng D F, Yan T B. *Diabetes Res. Clin. Pract.* 89 (1) (July 2010) 10-5; Pieber K, Herceg M, Paternostro-Sluga T. *J Rehabil Med* 42 (4) (2010) 289-95).

Some current research in animal models has shown that neurotrophin-3 can oppose the demyelination present in some peripheral neuropathies (Liu N, Varma S, Tsao D, Shooter E M, Tolwani R J. *J. Neurosci. Res.* 85 (13) (2007) 2863-9).

It is often the case that the disease that is causing the pain itself becomes untreatable and the main focus of care is then altered to be palliative. For example when a patient is suffering from chronic pain caused by terminal cancer the only treatment option available is the relief of pain. Unfortunately up to 40% of cancer sufferers have unmet needs in pain suppression at the present time.

More problems arise in the case of painful polyneuropathy, having both motor and sensory involvement, the estimated prevalence of which is 2%-3% in the general population and as high as 8% in people over the age of 55 years (England J D, Asbury A K. Lancet 363 (2004) 2151-2161).

Polyneuropathy is the simultaneous malfunction of many peripheral nerves throughout the body. Like peripheral neuropathy, polyneuropathy may be acute (beginning suddenly) or chronic (developing gradually, often over months or years) and may have several same or similar causes.

Neuropathic pain (NP) and painful polyneuropathies (PPs) are not synonymous; pain management specialists consider NP to result from many types of dysfunction within the sensory nervous system or its central connections (D. L. Menkes, A Practical Approach to the Treatment of Painful Polyneuropathies, in: T. E. Bertorini (Ed.), Neuromuscular Disorders: Treatment and Management, Chapter 6, Elsevier, 2011 (ISBN 978-1-4377-0372-6)).

Painful polyneuropathies, i.e. the simultaneous malfunction of many peripheral nerves throughout the body, are characterized by severe symptoms (http://www.merckmanuals.com/home/brain_spinal_cord_and_nerve_disorders/peripheral_nerve_disorders/polyneuropathy.html).

Acute polyneuropathy (for example, as occurs in Guillain-Barré syndrome) begins suddenly in both legs and progresses rapidly upward to the arms. Symptoms include weakness and a pins-and-needles sensation or loss of sensation. The muscles that control breathing may be affected, resulting in respiratory failure.

In the most common form of chronic polyneuropathy, only sensation is affected. Usually, the feet are affected first, but sometimes the hands are. A pins-and-needles sensation, numbness, burning pain, and loss of vibration sense and position sense (knowing where the arms and legs are) are prominent symptoms. Because position sense is lost, walking and even standing become unsteady. Consequently, muscles may not be used. Eventually, they may weaken and waste away.

Diabetic neuropathy commonly causes painful tingling or burning sensations in the hands and feet—a condition called distal polyneuropathy. Pain is often worse at night and may be aggravated by touch or by a change in temperature. People may lose the senses of temperature and pain, so they often burn themselves and develop open sores caused by prolonged pressure or other injuries. Without pain as a warning of too much stress, joints are susceptible to injuries. This type of injury is called Charcot's joints.

Polyneuropathy often affects the nerves of the autonomic nervous system, which controls involuntary functions in the body (such as blood pressure, heart rate, digestion, salivation, and urination). Typical symptoms are constipation, loss of bowel or bladder control (leading to fecal or urinary incontinence), sexual dysfunction, and fluctuating blood pressure—most notably a sudden fall in blood pressure when a person stands up (orthostatic hypotension). The skin may become pale and dry, and sweating may be reduced.

People who have a hereditary form may have hammer toes, high arches, and a curved spine (scoliosis). Abnormalities in sensation and muscle weakness may be mild. Affected people may not notice these symptoms or may consider them unimportant.

How completely people recover depends on the cause of polyneuropathy.

There are over 100 known acquired and inherited disorders that may cause polyneuropathy, a fact that presents challenges and can contribute to uncertainty about the scope, direction, and level of aggressiveness of any evaluation.

Several pharmaceuticals like anti-infectious medications, such as chloroquine, dapsone, isoniazid, metronidazole, nitrofurantoin, dideoxycytidine and other nucleoside analogs, chemotherapy and anticancer medications such as cisplatinum, taxanes (paclitaxel and docetaxel), suramin, thalidomide, vincristine, bortezomib, antirheumatic and immunosuppressants such as chloroquine and colchicine, cardiovascular medications such as amiodarone, hydralazine, perhexiline, propafenone; psychiatric and sedatives such as disulfiram and some other medications, such as pyridoxine (vitamin B6) and phenytoin, used for treating various disorders, including painful diseases, may cause painful polyneuropathies (T. M. Burns, M. L. Maueremann, Clinical Practice 76 (Suppl. 2) (2011) S6-S13).

Among the most important toxic agents causing polyneuropathy, especially neuropathic pain, are chemotherapeutic agents used for the treatment of neoplastic disease. Otherwise, painful polyneuropathy is a major complication of cancer treatment and is the main factor limiting the dosage of chemotherapeutics that can be administered to a patient (Macdonald, Neurologic Clinics 9 (1999) 955-967).

This is true for the commonly administered agents cisplatin, paclitaxel and vincristine (Broun, et al., Am. J. Clin. Oncol. 16:18-21 (1993); Macdonald, Neurologic Clinics 9 955-967 (1991); Casey, et al., Brain 96 69-86 (1973)). The identification of methods for preventing or alleviating dose-limiting painful polyneuropathic side effects would allow higher, and more therapeutically effective doses of these chemotherapeutics to be administered to patients, i.e., the therapeutic efficacy of such chemotherapeutics is typically a function of dose and therefore, increasing dosage provides increased patient survival (Macdonald, Neurologic Clinics 9 955-967 (1991); Oxols, Seminars in Oncology 16, suppl. 6:22-30 (1989)).

Beyond the potential for increasing the effectiveness of cancer chemotherapy, the identification of new methods for treating painful polyneuropathy has obvious value in alleviating the suffering of patients with a wide variety of systemic diseases and genetic conditions as well as therapeutic conditions.

The caregiver's requirements are to provide the patient with a sufficient dose of medication to allow them to be freed as far as possible from their pain but there are inherent problems with this.

Some drugs that are usually not considered pain relievers can lessen pain due to nerve damage. They include the antidepressant amitriptyline, the anticonvulsant gabapentin, and mexiletine (used to treat abnormal heart rhythms). Lidocaine, an anesthetic applied as a lotion, an ointment, or a skin patch, may also help.

Physicians and nurses are often reluctant to give large doses of analgesic drugs, even to dying patients. Their fear is that the large doses provided will lead to sedation or respiratory depression. The result of this can be that the patient's pain is not adequately cared for. It has also been recognized that a substantial proportion of patients, particularly those in minority groups, are receiving inadequate analgesic treatment.

It is often difficult to treat painful polyneuropathy with analgesics which are effective in common nociceptive pain, such as narcotic analgesics, antiinflammatory analgesics (The Lancet, vol. 353, pp. 1959-1966, 1999). For example, it is known that morphine has a potent analgesic effect on acute nociceptive pain, but does not exhibit a sufficient effect on neuropathic pain.

Further, it is also known that a nonsteroidal antiinflammatory analgesic has almost no effect on painful polyneuropathy (The Lancet, vol. 353, pp. 1959-1966, 1999 and Journal of Clinical and Experimental Medicine 203 (1) (2002) 65-69). This is attributable to the fact that the onset of pathogenic conditions of neuropathic pain is different from that of inflammatory pain. That is, inflammatory pain is induced by the activation of sensory receptors (nociceptors) in normal somatosensory nerve. The activation is caused by noxious stimulus such as inflammatory chemical mediators released after tissue injury, disease, or inflammation (The Clinical Journal of Pain, 16 (2000) S131-S138). Antiinflammatory analgesics exhibit an analgesic effect by suppressing the production of inflammatory chemical mediators. On the other hand, neuropathic pain is defined by IASP as "pain initiated or caused by a primary lesion or dysfunction in the nervous system" (Classification of Chronic Pain, International Association for the Study of Pain (IASP) Task Force on Taxonomy IASP Press: Seattle, pp. 209-214, 1994).

Further, the insufficient analgesic effect of morphine is a major characteristic of neuropathic pain, therefore, it is also used for the diagnosis of neuropathic pain (Journal of Clinical and Experimental Medicine, 189 (10) (1999) 751-755).

As a method for treating painful polyneuropathy, neurosurgical interventions such as nerve block or spinal epidural electric stimulation (Journal of Clinical and Experimental Medicine, 189 (10) (1999) 757-762), pharmacological interventions such as antidepressants (Clinics and Drug Therapy, 18 (7) (1999) 643-646), antiepileptic agents (Clinical Theraputics, 25 (2003) 2506-2538), or the like are employed.

Tricyclic antidepressants appear to be the most efficacious treatment of painful polyneuropathy. However, these drugs are contraindicated in some patients and a substantial number of patients decline treatment due to side-effects. Therefore, effective drugs that are better tolerated are needed. Clinical and basic research has demonstrated that drugs with serotonergic action such as escitalopram can alleviate neuropathic pain and it is tested if it would relieve painful polyneuropathy (ClinicalTrials.gov, a service of the US National Institute of Health—http://clinicaltrials.gov/ct2/show/NCT00162968)

A major disadvantage with the currently available drug therapies to treat severe painful polyneuropathy can be that the use of opioid based drugs result in the patient becoming drowsy and unresponsive, and may lead to unwanted side effects including constipation, sedation, pruritis, nausea and vomiting, respiratory depression, dysphoria and hallucinations and urinary retention. Increased dosages of these medicaments can also cause respiratory failure and in consequence may result in premature death.

Furthermore, this painful polyneuropathy treatment is applicable only in adults, i.e. those 18 years and older. As such, these data cannot be used to guide treatment decisions in younger individuals. Medications used in the pediatric population should be adjusted for the patient's age, height, and weight and should be prescribed by pediatric neurologists who specialize in the treatment of painful polyneuropathy in children.

Thus, satisfactory treatment methods in terms of the efficacy and safety have not been established, and the development of more efficacious therapeutic agents in painful polyneuropathy is urgently desired.

The natural and synthetic aluminosilicates, known for their strong adsorption potential, have been extensively used in technical applications as an adsorbent, as food and beverage supplements in animal and human feed, as vehicles to carry low molecular bio-active substances and macromolecules such as proteins into viable cells (Journal of Biotechnology 111 (2004) 279-290)), as valuable ingredients of therapeutic compositions in human and veterinary medicine, and for the treatment of several diseases including cancer (*Journal of Colloid and Interface Science*, In Press, Corrected Proof, Available online 10 Sep. 2011) and disease side-effects such as pain (WO 2011/007794 A1).

WO 01/95920 and WO 03/013563 describe the use of zeolite preparations for the treatment of neuropathy in patients suffering from diabetes.

However, diabetic neuropathy is caused by a dysfunction of metabolic pathways related to the increased blood glucose levels. For example, the reduced detoxification of the nerve cells, the accumulation of fructose and sorbitol in the cells, which results in osmotic damage to the cells, and the inhibition of certain cellular enzymes, are known to cause nerve damage. Furthermore, microangiopathy (narrowing of capillaries that provide oxygen to the nerve cells) which results in a lack of oxygen (hypoxia) in the nerve cells, causing their dysfunction and eventual cell death, and impairment of the energy balance of the cell are known as a further cause of diabetic neuropathy. In contrast, chemotherapeutic agents directly damage the axons and/or myelin sheath of the nerve cells and thereby inhibit the axoplasmatic transport in nerve cells, i.e. these agents directly cause neuropathy.

Additionally, treatments which are known to be effective for the treatment of diabetic neuropathy were found not to be useful in treating polyneuropathy caused by toxic substances. For example, carbamazepin and gabapentin (both being anticonvulsive agents) have been found to be ineffective to control polyneuropathy caused by toxic substances. However, the use of these antidepressants and anticonvulsive agents has been proven to be useful to reduce the pain intensity in patients with diabetic neuropathy.

The fact that measures exist to control neuropathic pain in diabetes but that no adequate measures exist to control polyneuropathy caused by toxic agents illustrates that a treatment known to be effective for one type of polyneuropathy is not automatically successful when treating another type of polyneuropathy.

Therefore, the effectiveness of aluminosilicates in the prevention or treatment of painful polyneuropathies, the simultaneous malfunction of many peripheral nerves throughout the body, caused by toxic agents like drugs, organic metals, heavy metals, excess intake of vitamin $B_6$ (pyridoxine), particularly by the administration of a chemotherapeutic cytotoxic agent, has not been previously known.

DISCLOSURE OF THE INVENTION

Problem to be Solved by the Invention

An object of the present invention is to provide new means for preventing or treating a painful polyneuropathy in a patient, wherein the polyneuropathy is caused by a toxic agent.

In particular, the means are to prevent, reduce or eliminate the symptoms associated with the painful polyneuropathy, such as neuropathic pain.

Preferably, the means are to be more effective and/or have fewer side-effects than known means for preventing or treating such polyneuropathy, such as narcotic analgesics.

SUMMARY OF THE INVENTION

The inventors' studies towards achieving the above objects unexpectedly found that an aluminosilicate exhibits a remarkable therapeutic effect to prevent, reduce or eliminate the symptoms associated with the simultaneous malfunction of many peripheral nerves throughout the body, known as painful polyneuropathy, caused by exposition of a patient to toxic agents.

Thus, in order to solve the above problems, the invention provides:

An aluminosilicate for use in a method of preventing or treating a painful polyneuropathy in a patient, wherein the polyneuropathy is caused by a toxic agent.

A pharmaceutical composition comprising an effective amount of an aluminosilicate as an active ingredient and a pharmaceutically acceptable carrier for preventing or treating a painful polyneuropathy in a patient, wherein the polyneuropathy is caused by a toxic agent.

A method of preventing or treating a painful polyneuropathy in a patient, wherein the polyneuropathy is caused by a toxic agent and the method comprises administering to the patent an effective amount of an aluminosilicate before, simultaneously with or after exposition of the patient to the toxic agent.

A commercial package including a pharmaceutical composition containing an aluminosilicate as an active ingredient, and a description that the aluminosilicate can be used or should be used for preventing or treating a painful polyneuropathy in a patient, wherein the polyneuropathy is caused by a toxic agent.

DETAILED DESCRIPTION OF THE INVENTION

In the context of the present invention, a painful polyneuropathy is a simultaneous malfunction of many peripheral nerves throughout the body. It is also known as peripheral neuropathy. A key symptom of painful polyneuropathy is neuropathic pain. The invention achieves, in particular, a prevention, reduction or elimination of neuropathic pain caused by a toxic agent. The polyneuropathy may be acute (beginning suddenly) or chronic (developing gradually, often over months or years).

The aluminosilicate used according to the invention may be a zeolite. The zeolite may be a natural zeolite or a synthetic zeolite. The aluminosilicate may also be an aluminosilicate derivative.

The natural zeolite may be, for example, clinoptilolite, silver zeolite, mordenite, phillipsite, analcite. Clinoptilolite is particularly preferred.

Synthetic zeolites may be, for example, zeolite A, zeolite W, zeolite X.

The aluminosilicates used according to the invention are known as such and can be easily obtained by known production methods and/or are commercially available.

The polyneuropathy to be prevented or treated according to the invention is caused by a toxic agent.

The toxic agent may be, for example, a drug, a natural or synthetic toxin, a heavy metal, excess vitamin B6 (pyridoxine), ethyl alcohol.

The drug may be, for example, one of the following: Pharmaceuticals such as anti-infectious medications, chemotherapy and anticancer medications, antirheumatic and immunosuppressants such as chloroquine and colchicine, cardiovascular medications such as amiodarone, hydralazine, perhexiline, propafenone; psychiatric and sedatives such as disulfiram and some other medications, such as pyridoxine (vitamin B6), phenytoin, nitrofurantoin, isoniazid, fluoroquinolones.

In particular, the toxic agent may be a chemotherapeutic cytotoxic agent.

Anti-infectious medications may be, for example, chloroquine, dapsone, isoniazid, metronidazole, nitrofurantoin, dideoxycytidine and other nucleoside analogs, fluoroquinolone antibiotics and other anti-infectives causing painful polyneuropathies.

Chemotherapy and anticancer medications may be, for example, alkylating agents, anti-metabolites, plant alkaloids and terpenoids, topoisomerase inhibitors, cytotoxic antibiotics and other anticancer therapeutics causing painful polyneuropathies.

Alkylating agents may be, for example, platinum drugs such as cisplatin and carboplatin, oxaliplatin, and other platinum drugs, and other alkylating agents such as mechlorethamine, cyclophosphamide, chlorambucil, ifosfamide, and other alkylating agents causing painful polyneuropathies.

Plant alkaloids and terpenoids are derived from plants and block cell division by preventing microtubule function. Microtubules are vital for cell division, and, without them, cell division cannot occur. The main examples are vinca alkaloids such as vincristine, vinblastine, vinorelbine and vindesine; podophyllotoxin and taxanes such as the natural product paclitaxel, originally known as Taxol and first derived from the bark of the Pacific Yew tree, its semi-synthetic analogues such as docetaxel, and other plant alkaloids and terpenoids causing painful polyneuropathies.

Topoisomerase inhibitors may be, for example, inhibitors of type I such as camptothecins, i.e. irinotecan and topotecan, and type II inhibitors such as semisynthetic derivatives of epipodophyllotoxins, i.e amsacrine, etoposide, etoposide phosphate, and teniposide, and other topoisomerase inhibitors causing painful polyneuropathies.

Cytotoxic antibiotics may be, for example, actinomycin, anthracyclines such as doxorubicin, daunorubicin, valrubicin, idarubicin, epirubicin, which also inhibit topoisomerase II, and other cytotoxic antibiotics such as bleomycin, plicamycin, mitomycin and other cytotoxic antibiotics causing painful polyneuropathies.

Other anticancer therapeutics may be, for example, suramin, thalidomide, bortezomib.

A pharmaceutical composition for use according to the invention can be prepared by common procedures using a conventional pharmaceutical carrier, excipient, or the like. The composition may be solid or liquid.

The administration of the aluminosilicate to the patient may be oral administration, for example in the form of a tablet, a pill, a capsule, a granule, a powder, or a liquid suspension.

As a solid composition for oral administration according to the invention, a tablet, a powder, a granule, or the like may be used. In such a solid composition, one or more active ingredients are mixed with at least one inert diluent such as lactose, mannitol, glucose, hydroxypropyl cellulose, microcrystalline cellulose, starch, polyvinylpyrrolidone, and/or magnesium metasilicate aluminate. The composition may contain an additive other than the inert diluent, for example, a lubricant such as magnesium stearate, a disintegrating agent such as cellulose calcium glycolate, a stabilizing agent, or a solubilizing agent according to a common procedure. The tablet or pill may be coated with a sugar coating such as sucrose, gelatin, hydroxypropyl cellulose, hydroxypropylmethyl cellulose phthalate, or the like, or a film such as a gastric-soluble or enteric-soluble substance, as needed.

A liquid composition for oral administration includes a pharmaceutically acceptable suspension, and the like, and contains a commonly used inert diluent such as purified water or ethanol. The liquid composition may further contain an auxiliary agent such as a wetting agent, or a suspending agent, a sweetener, a flavor, a perfume, or a preservative other than the inert diluent.

According to the invention, an aluminosilicate, preferably a natural or synthetic zeolite, more preferably clinoptilolite, is administered to a patient with painful polyneuropathy. A suitable oral daily dose ranges from about 0.01 to 1000 mg/kg of body weight, preferably from about 0.1 to 500 mg/kg of body weight, more preferably from about 10 to 100 mg/kg of body weight. The daily dose is administered once per day or two to four times per day by dividing it into two to four portions. The dose is appropriately determined depending on the individual patient by taking into consideration the symptoms, age, sex, and the like.

The patient is preferably a human. The patient may be, in particular, a patient undergoing anticancer chemotherapy.

The aluminosilicate, preferably a natural or synthetic zeolite, more preferably clinoptilolite, may be administered, in particular, to a patient with painful polyneuropathy caused by a toxic agent, such as a chemotherapy or anticancer medication, where the analgesic effect of a narcotic analgesic such as morphine is insufficient.

The aluminosilicate may be administered to the patient before, simultaneously with or after exposition of the patient to the toxic agent that causes the painful polyneuropathy.

The administration of an aluminosilicate, preferably a natural or synthetic zeolite, more preferably clinoptilolite, according to the invention provides excellent effects in preventing or treating a painful polyneuropathy caused by a toxic agent, i.e. in preventing, reducing or eliminating the symptoms of that polyneuropathy, especially when the toxic agent is one of the following: drugs such as anti-infectious medications, chemotherapy and anticancer medications, antirheumatic and immunosuppressants such as chloroquine and colchicine, cardiovascular medications such as amiodarone, hydralazine, perhexiline, propafenone; psychiatric and sedatives such as disulfiram and some other medications, such as pyridoxine (vitamin B6) and phenytoin, more preferably chemotherapy and anticancer medications such as alkylating agents from the group of platinum drugs, i.e. cisplatin and carboplatin, oxaliplatin, anti-metabolites, plant alkaloids and terpenoids, such as vinca alkaloids, i.e. vincristine, vinblastine, vinorelbine and vindesine, taxanes, i.e paclitaxel, and its semi-synthetic analogues such as docetaxel, topoisomerase inhibitors, cytotoxic antibiotics and other anticancer therapeutics such as suramin, thalidomide, bortezomib, causing painful polyneuropathies.

The present invention is illustrated by the following non-limiting example.

EXAMPLE

A long-term post-marketing observational study on the improvement of peripheral neuropathy as a side effect of chemotherapy by adjuvant administration of activated natural zeolite clinoptilolite involving more than 2,000 patients was carried out.

150 randomized patient records were evaluated over the entire observation period; the known medical benchmark for subjective criteria with respect to the general side-effects of chemotherapy and the corresponding laboratory test results served as a reference.

In summary, patients reported that after taking activated zeolite, the stressful disturbances of skin sensation they had been experiencing were noticeably improved.

The invention claimed is:

1. A method for preventing or treating a painful polyneuropathy in a human patient comprising administering an aluminosilicate to the patient, wherein the polyneuropathy is caused by a toxic agent.

2. The method of claim 1, wherein neuropathic pain is prevented, reduced or eliminated.

3. The method of claim 1, wherein the aluminosilicate is a natural zeolite or a synthetic zeolite.

4. The method of claim 3, wherein the natural zeolite is selected from the group consisting of clinoptilolite, silver zeolite, mordenite, phillipsite, analcite and mixtures thereof.

5. The method of claim 3, wherein the synthetic zeolite is selected from the group consisting of zeolite A, zeolite W, zeolite X and mixtures thereof.

6. The method of claim 1, wherein the toxic agent is a drug, a natural or synthetic toxin, a heavy metal, or excess pyridoxine.

7. The method of claim 1, wherein the toxic agent is selected from the group consisting of anti-infectious medications, chemotherapy or anticancer medications, antirheumatics, immunosuppressants, cardiovascular medications, psychiatric medications and sedatives.

8. The method of claim 1, wherein the toxic agent is selected from the group consisting of chloroquine, colchicine, amiodarone, hydralazine, perhexiline, propafenone, disulfiram, pyridoxine and phenytoin.

9. The method of claim 1, wherein the toxic agent is selected from the group consisting of alkylating agents of the group of platinum drugs, anti-metabolites, plant alkaloids and terpenoids, taxanes, topoisomerase inhibitors, and cytotoxic antibiotics.

10. The method of claim 1, wherein the toxic agent is selected from the group consisting of cisplatin and carboplatin, oxaliplatin, vincristine, vinblastine, vinorelbine and vindesine, paclitaxel, docetaxel, suramin, thalidomide, and bortezomib.

11. The method of claim 1, wherein the toxic agent is a chemotherapeutic cytotoxic agent.

12. The method of claim 1, wherein the patient is a human undergoing anticancer chemotherapy.

13. A method for preventing or treating a painful polyneuropathy in a human patient comprising administering a pharmaceutical composition comprising an effective amount of an aluminosilicate as an active ingredient and a pharmaceutically acceptable carrier to the patient, wherein the polyneuropathy is caused by a toxic agent.

* * * * *